(12) United States Patent
Manser et al.

(10) Patent No.: US 8,262,995 B2
(45) Date of Patent: Sep. 11, 2012

(54) SYSTEM WITH A PLUGGABLE DATA TRANSFER MODULE WHICH TRANSFERS DATA FROM AN ANALYTICAL SYSTEM TO A DATA PROCESSING UNIT

(75) Inventors: Udo Manser, Wiesloch (DE); Dieter Schaefer, Schriesheim (DE); Michael Schabbach, Weinheim (DE); Peter Kuenstler, Bammental (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1494 days.

(21) Appl. No.: 10/316,774

(22) Filed: Dec. 11, 2002

(65) Prior Publication Data

US 2003/0139653 A1 Jul. 24, 2003

(30) Foreign Application Priority Data

Dec. 22, 2001 (DE) ................................ 101 63 774

(51) Int. Cl.
*G01N 15/06* (2006.01)
*G01N 33/00* (2006.01)
*G01N 33/48* (2006.01)

(52) U.S. Cl. ........ 422/68.1; 422/82.01; 422/50; 422/61; 422/63; 422/80; 422/81; 422/82.02; 422/502; 422/503; 436/43; 436/149; 436/150; 600/300; 600/301; 600/347; 600/365

(58) Field of Classification Search .......... 600/300–301, 600/347, 365; 128/903–905; 422/68.1, 82.01; 436/149, 150

See application file for complete search history.

(56) References Cited

U.S. PATENT DOCUMENTS

| | | | |
|---|---|---|---|
| 5,366,609 A | 11/1994 | White et al. | |
| 5,428,677 A * | 6/1995 | Hakamada | 379/114.18 |
| 5,636,264 A | 6/1997 | Sulavuori et al. | 379/56 |
| 5,777,903 A | 7/1998 | Piosenka et al. | 364/700 |
| 5,805,416 A | 9/1998 | Friend et al. | |
| 5,931,791 A | 8/1999 | Saltzstein et al. | |
| 6,171,264 B1 | 1/2001 | Bader | |
| 6,398,116 B1 * | 6/2002 | Kreft | 235/492 |
| 6,558,320 B1 * | 5/2003 | Causey et al. | 600/300 |
| 2002/0103435 A1 * | 8/2002 | Mault | 600/439 |
| 2003/0114836 A1 | 6/2003 | Estes et al. | |
| 2004/0167464 A1 | 8/2004 | Ireland et al. | |
| 2007/0060869 A1 | 3/2007 | Tolle et al. | |

(Continued)

FOREIGN PATENT DOCUMENTS

DE 4305058 A1 8/1994

(Continued)

OTHER PUBLICATIONS

German Search Report dated Aug. 18, 2010 in related German patent application (English translation of the report is attached) 5 pages.

*Primary Examiner* — Brian J Sines
(74) *Attorney, Agent, or Firm* — Barnes & Thornburg, LLP

(57) ABSTRACT

The invention concerns a pluggable data transfer module and a method that can be used to transfer data from an analytical system to a data processing unit in a galvanically decoupled manner. This invention is particularly suitable for medical fields of application in which recently it has become more and more desirable to process analytical data of a patient.

19 Claims, 2 Drawing Sheets

U.S. PATENT DOCUMENTS

2007/0060870 A1    3/2007    Tolle et al.

FOREIGN PATENT DOCUMENTS

| | | |
|---|---|---|
| DE | 4415896 A1 | 11/1995 |
| DE | 19703854 A1 | 8/1998 |
| EP | 0622935 A1 | 11/1994 |
| EP | 0665655 A2 | 8/1995 |
| EP | 0790749 A2 | 8/1997 |
| EP | 1177802 A1 | 2/2002 |
| EP | 1759726 A2 | 3/2007 |
| JP | 59011478 | 1/1984 |
| JP | 59011478 A | 1/1984 |
| JP | 10305016 | 11/1998 |
| JP | 10315509 | 12/1998 |
| JP | 2000148317 A | 5/2000 |
| JP | 57119176 | 3/2007 |
| WO | WO 95/24233 | 9/1995 |
| WO | WO 95/24333 | 9/1995 |
| WO | WO 98/58510 | 12/1998 |
| WO | WO 99/60713 | 11/1999 |
| WO | WO 00/45696 | 8/2000 |
| WO | WO 00/74752 A1 | 12/2000 |
| WO | WO 01/82063 A1 | 11/2001 |

* cited by examiner

SYSTEM WITH A PLUGGABLE DATA TRANSFER MODULE WHICH TRANSFERS DATA FROM AN ANALYTICAL SYSTEM TO A DATA PROCESSING UNIT

TECHNICAL FIELD

The invention concerns a system with a pluggable data transfer module which converts electrical data from an analytical system and transfers these converted data in a galvanically decoupled form to a data processing unit. Hence the present invention relates to the field of data transfer.

BACKGROUND

Recently such data transfer between an analytical system and a data processing unit has proven to be increasingly useful since it is often desirable to process analytical data which for example simplifies a continuous monitoring of analytical data. A continuous monitoring of analytical data or for example a statistical evaluation of these data are only a few possibilities for optimizing an analytical process or its application.

Although data processing offers various advantages, it often proves to be too voluminous to be performed by conventional analytical instruments alone. Consequently additional constructional measures would be required to implement data processing by means of an analytical system which would increase the manufacturing costs. Hence a data processing unit is often not integrated into the analytical system for cost reasons and separate data processing units such as a PC are used instead. One of the advantages of this is that a data processing unit does not need to be integrated as a standard feature and thus the manufacturing costs of analytical instruments for fields of application in which data processing is not required are not unnecessarily increased. One field of application in which a reduction of manufacturing costs is important is for example the medical field. This applies in particular to the medical field of application in which the analytical instruments are intended for personal use. The reason for this is that the selling price is an important buying criterion for analytical systems that are sold to private individuals.

Despite the problems of cost effective instrument manufacture, the ability to process data will become more and more indispensable in the future since processing and evaluation of analytical data often proves to be useful particularly in the medical field.

This should simplify and improve monitoring of the state of health and optimization of treatments for private individuals.

In practice it turns out that, one the one hand, especially modern patients desire an autonomous management of their analytical data for an independent and optimized handling of their disease but, on the other hand, data processing is often unused since the operators of analytical instruments are often elderly persons who are not familiar with the modern methods of data processing.

Hence it is desirable to firstly only offer customers the possibility of data processing without incurring additional costs. With respect to further cost reduction the data processing should not only be carried out externally but instrument components for data processing that are already present integrated into the analytical instrument should be excluded from the analytical instrument. Such an instrument component is for example used to transfer data from the analytical instrument to an external data processing unit. Such a data transfer module is offered separately to the customer as an additional component and can be connected to the analytical instrument when required. This enables the operator to decide for himself whether to incur additional costs for his own data processing.

However, the provision of a separate data processing unit as an additional component of an analytical instrument requires that the connection of the data processing unit to the analytical instrument is simple to handle. Furthermore such a connection of a data transfer module should be inexpensive and not require complicated constructional measures, e.g. on the analytical instrument, so that the offer of an additional data processing remains attractive. An inexpensive connection of a data transfer module is disclosed in the prior art which utilizes a calibration module interface, which is usually already present as an interface, for a data transfer module.

A calibration module interface on an analytical system is used to connect a so-called calibration module. The calibration module contains coding which is stored on a chip and whose data are used to calibrate measuring data of an analytical instrument. Such a calibration is for example used to compensate for lot variations in the reagent system.

Examples of such systems are known from Roche Diagnostics GmbH which are used to measure blood sugar (AccuChek Advantage Family®). With such a glucose measuring instrument glucose is determined by means of test strips on which a sample is applied. The sample reacts with a reagent system of the test strip in such a manner that the glucose content of the sample can be quantified by the analytical instrument. The aforementioned calibration module which is often referred to as a codekey is for example enclosed in a pack of test strips in order to allow for lot-to-lot variations which occur in the manufacture of the test strips. For this purpose the calibration module is connected to the interface that is provided and the coding stored on a chip can be read out. The measured data are corrected in the analytical instrument by means of the coding.

In order to transfer data between the analytical instrument and a data processing unit the calibration module is removed in the prior art from the interface such that the interface can be used for data transfer. For this purpose a data transfer cable is used in the interface. The previously measured and stored data are transferred to the data processing unit by means of the data transfer cable by for example connecting the data transfer cable to a PC. The data can then for example be transferred by means of the PC software CAMIT® from Roche Diagnostics GmbH.

Suitable cables which can communicate with a calibration module interface are for example provided by Roche Diagnostics GmbH under the name "AccuChek Interface Cable®" or "Professional Cable®".

However, a disadvantage of the prior art is that an electrical contact has to be made between the analytical instrument and the mains voltage of the data transfer unit for the data transfer. There is a potential risk to the customer that he may come into contact with the mains voltage via the contact chain: mains voltage-PC-analytical instrument-test strips-blood drop-user.

Hence when using such analytical instruments it is often noted in the manual that there is a risk to the user of electrification by the data transfer cable which is connected to the data processing unit which requires special precautionary measures in its operation.

SUMMARY

The object of the invention is to design an analytical system with a pluggable data transfer module which allows a convenient, economical and reliable evaluation of analytical data.

In particular electrical contact with the data processing unit should be avoided during the transfer of data.

The invention concerns a pluggable data transfer module which contains an interface which is compatible with a calibration module interface of an analytical instrument and allows data transfer of electrical signals between the data transfer module and the analytical instrument. The data transfer module additionally contains a converting unit which converts the electrical signals into electromagnetic or acoustic signals or converts electromagnetic or acoustic signals into electrical signals, and a communication unit which allows the data transfer of electromagnetic or acoustic signals between the data transfer module and a data processing unit.

Electromagnetic signals in the sense of the invention are for example optical signals.

Another aspect of the invention is an analytical system with a pluggable data transfer module which transfers data from an analytical instrument to a data processing unit comprising an analytical instrument having an interface to which a calibration module or, alternatively a pluggable data transfer module can be attached, and a pluggable data transfer module. The data transfer module has an interface which allows data transfer of electrical signals between the data transfer module and the interface of the analytical instrument. The electrical signals are converted into electromagnetic or acoustic signals, or electromagnetic or acoustic signals are converted into electrical signals with the aid of a converting unit.

Consequently a converting unit in the sense of the invention can convert electrical signals into acoustic signals as well as into electromagnetic signals as required. However, it is also conceivable that a conversion of electrical signals into exclusively acoustic or electromagnetic signals is sufficient and hence the module is only suitable for one type of signal conversion. Irrespective of the type of signal conversion, a signal conversion usually comprises the ability to convert electrical signals into non-electrical signals and the complementary path of transforming non-electrical signals into electrical signals. A simplified embodiment which only allows one direction of signal conversion and does not allow the complementary direction is of course conceivable independent of the respective field of application.

A communication unit enables data transfer of the electromagnetic or acoustic data between the data transfer module and a data processing unit.

Hence the invention simplifies the handling for the user by means of a pluggable contact which ensures a rapid connection of the data transfer module to an analytical instrument. In this manner data from the analytical instrument can be exchanged with the data transfer module via the interface. The data transfer module converts the signals. This enables data to be exchanged between the data transfer module and data processing unit which ensures galvanically decoupled data transfer. There is no risk to the user that he may for example come into contact with the mains voltage of a PC. Other handling advantages are due to the fact that data transfer occurs through space and no connection is necessary, for example by a cable, between the data transfer module and the data processing unit.

An infrared module may for example be integrated into the data transfer module which is suitable for transmitting and receiving IR radiation such that data can be transferred by means of an IR transmitter to the data processing unit. The data transfer module is then able to convert electrical signals into IR signals or to convert IR signals into electrical signals. The data processing unit detects the signals for example by means of an IR receiver. The IR module can be advantageously be constructed such that the signals can be detected by commercial IR receiver/transmitting units such as those that are for example used on PCs. Hence data can be transferred over a spatial distance of ca. 1 m with commercial transmitter/receiver power.

The use of a microcontroller has proven to be particularly suitable under the said conditions and offers space, cost and functional advantages for the data transfer module such that for example the required circuits, impulse modulation and automatic voltage cut-out are integrated in one component. This for example ensures that data transfer does not occur until the analytical instrument is ready to operate in order to prevent erroneous data transfer.

However, it is also possible to use a radio module which is suitable for transmitting and receiving RF signals. In this case electrical signals are converted into RF signals or RF signals are converted into electrical signals.

However, if one does not wish to be limited to one particular signal conversion in order to achieve a more diverse compatibility with data processing units, it is of course also possible to utilize any desired combination of signal-specific modules and signal converters. In this case a data transfer module would for example have an IR and an RF module.

In a preferred embodiment the analytical instrument is used, as already described as an example, to measure glucose concentrations that are determined using test elements. Since especially in the case of diabetes, glucose measurements are carried out several times per day, special analytical instruments for glucose measurement are manufactured for personal use. Diabetes is one of the main diseases where a good monitoring of the state of the disease is helpful to prevent damage such as loss of sight. Hence in this case there is a great demand for disease monitoring with the aid of a suitable data management which can be carried out by the patient as required.

Of course any type of analytical instrument is conceivable within the scope of the invention such as for example instruments for measuring coagulation.

In another preferred embodiment the analytical system contains a calibration module which is plugged into the interface of the analytical instrument. Such a calibration module (codekey) is usually included in the pack when for example buying test elements. The customer is then instructed to connect the calibration module with the analytical instrument via the interface so that the measured data can for example be corrected. The fact that the same interface of the analytical instrument is also suitable for connecting the instrument with the data transfer module avoids additional measures when constructing an analytical instrument. Hence the customer can decide on data processing at any time even if he did not take this into account when buying the analytical instrument since it is only necessary to subsequently purchase a data transfer module according to the invention.

The data transfer module preferably obtains its energy from the analytical system; but an energy supply unit may also be integrated into the data transfer module.

If radio technology is integrated in the data transfer module, it is also possible, in addition to the said energy supplies, to obtain energy from the instrument surroundings in the form of an energizing oscillation such that the data transfer module is a component of a transponder system. Transponder technology enables the module to obtain its energy passively from the instrument surroundings by means of the transmitter antennae of the reading system which continuously supplies energy to the transponder via an alternating magnetic field. Transponders are completely maintenance-free and have a long life span. It is preferable to use the low frequency range (124 kHz or 62 kHz) so that the data transfer module is not subject to any special safety requirements.

Another advantage of using a transponder is that data can be written on a microchip and hence this enables a reversible storage of data. Advantages of data storage are elucidated in more detail in the following.

As already described there are in general several ways for a data transfer module to be supplied with energy. Since the aforementioned analytical instruments in the medical field are often battery-operated instruments it is desirable to have a low energy consumption. This can for example be assisted by the data transfer module being used for as short a period as possible. In a preferred embodiment the data transfer module can be activated by contact with the instrument interface or by a start impulse of the data processing unit or of the analytical system. In a preferred embodiment the data transfer module is deactivated after a defined period without data transfer. This ensures that the data transfer module does not unnecessarily consume energy.

The transfer data can be processed with the aid of the data processing unit.

In another preferred embodiment the data transfer module contains a storage device which, as described above, can be realized in the form of a transponder system enabling for example stored data to be transferred from the analytical system to the data processing unit even without contact of the data transfer module. The data transfer module preferably automatically stores the transferred data which can subsequently be removed from the analytical instrument. The data transfer module is easy to transport due to its small size. Hence the user is able to read out the stored data at a selected site without having to also carry the analytical instrument. This is particularly suitable for users who are not familiar with modern methods of data transfer but who desire a monitoring of their data. Consequently the preferred embodiment of the invention enables an easy-to-handle data processing by persons who are not themselves able to process the data and who can thus commission someone else to carry out the data processing who is usually their attending physician. Hence the user does not have to deal with the steps of data processing which would otherwise be necessary such as transfer of the data by internet or storing the data on a storage medium etc.

Another aspect of the invention is a method for transferring data between an analytical system and a data processing unit.

The method comprises plugging a pluggable calibration module into an interface of the analytical system and unplugging it from the interface after transferring the calibration module data to the analytical system as well as plugging a pluggable data transfer module into the interface of the analytical system and transferring electrical signals of the analytical system to the data transfer module. Conversion of the electrical signals of the analytical system into electromagnetic or acoustic signals by means of the data transfer module and transfer of the converted data to a data processing unit.

In a preferred embodiment of the method a data transfer module or an analytical system as described above is used.

A preferred embodiment of the data transfer module is suitable for a method as described above and a preferred analytical system contains a data transfer module as described above.

BRIEF DESCRIPTION OF THE DRAWINGS

Some examples are elucidated in more detail on the basis of the following figures.

DETAILED DESCRIPTION OF THE DRAWINGS

Figure 1:
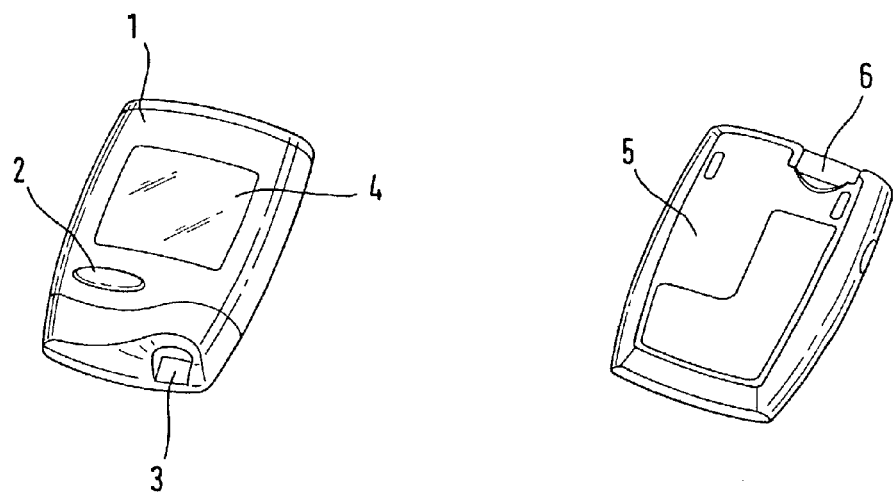
FIG. 1: analytical instrument for measuring glucose concentration—front and rear view.

FIG. 1 shows a front view (1) of a glucose measuring instrument which has an operating keyboard (2) and a slot for a test strip (3). After sample application a test strip is inserted into the slot (3) in order to measure the glucose value in the analytical instrument. The result of the measurement is displayed to the user by means of the display (4). The analytical instrument has another slot (6) on the rear side (5) to insert a calibration module. This calibration module is usually referred to as a codekey. Such a codekey is usually enclosed in a pack of test strips in order that the test strip chemistry can be taken into account when determining the concentration of glucose. This codekey contains a coding which allows the measured values to be corrected when calculating the concentration and takes into consideration lot-specific variations of the test strips. The instrument reads out the stored code and takes it into consideration in order to display a corrected measurement result on the screen. According to the invention the slot (6) can also be used to connect the analytical instrument with a data transfer module. After removing the codekey from the interface, the data transfer module can be plugged into the free interface.

Figure 2:
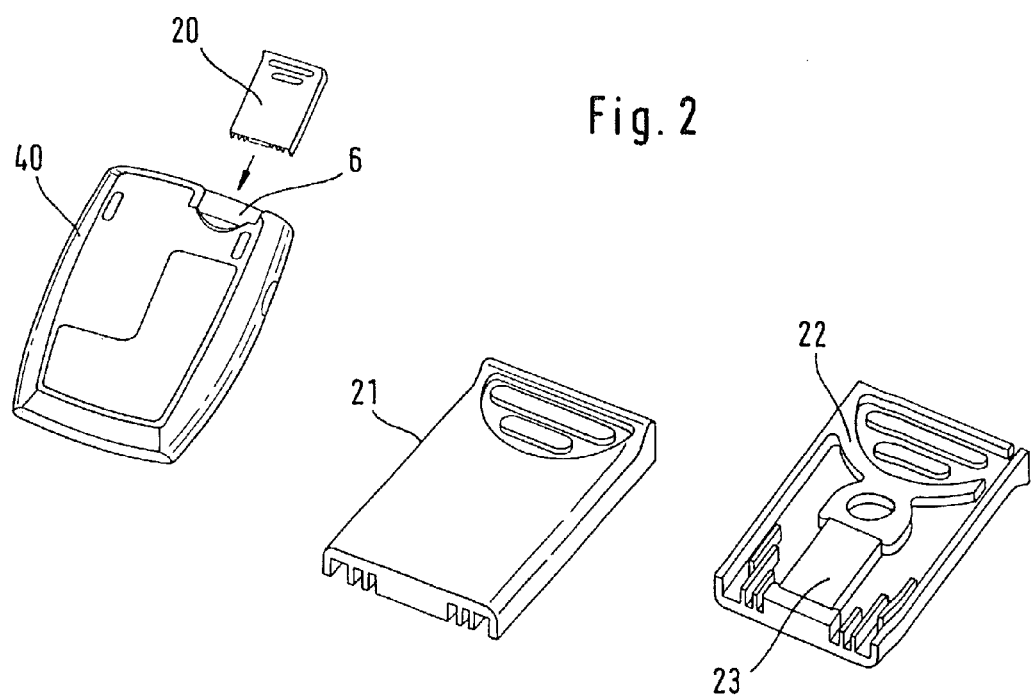
FIG. 2: analytical instrument with a codekey

FIG. 2 shows an example of an analytical instrument (40) having a codekey (20) that is contacted with the analytical instrument as is already known in the prior art.

The codekey has a plastic housing (22), a front view (21) of which is also shown in FIG. 2. The plastic housing is designed to be compatible with the slot (6) of the analytical instrument. The data of the codekey are stored on the chip (23) and can be read out by the analytical system after contacting the codekey.

Figure 3:
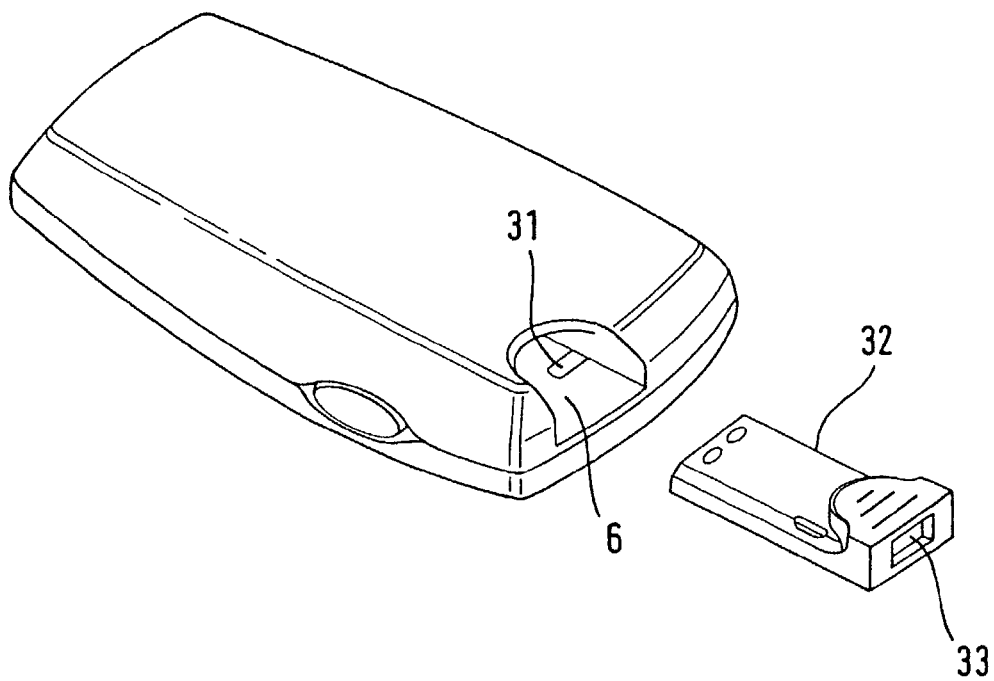
FIG. 3: analytical system comprising an analytical instrument and data transfer module

FIG. 3 is a detailed illustration of the slot (6) and also shows an example of an infrared data transfer module (32) which contains an infrared transmitter/receiver (33). After insertion of the data transfer module (32), the analytical module is in contact with the data transfer module via the contacts (31). The contact of the data transfer module with the analytical instrument automatically activates the data transfer module after a defined time period. Electronic signals of previously stored data on the analytical instrument are transferred via the interface (31) to the data transfer module. The infrared transfer module is now able to convert the electrical signals into infrared signals.

Figure 4:
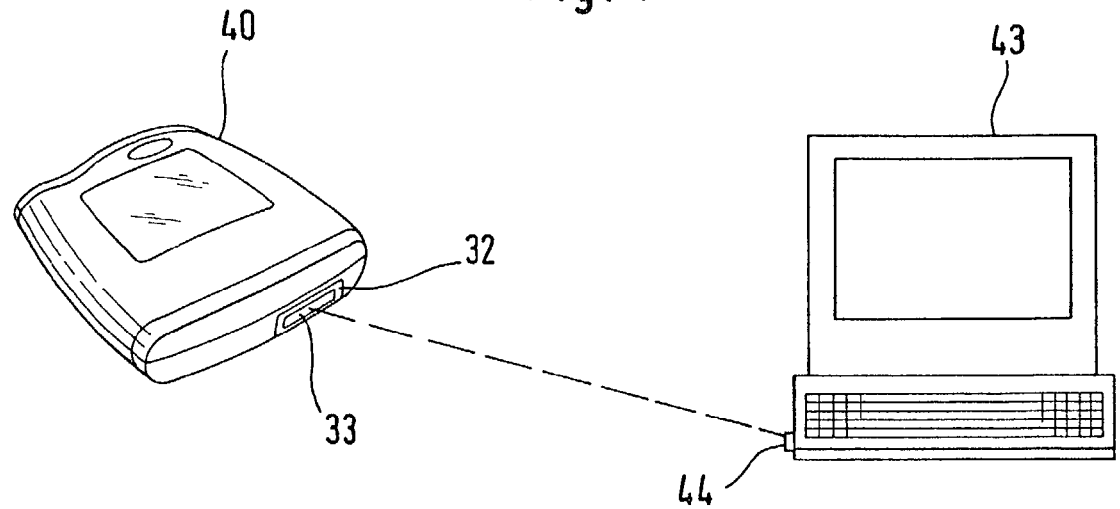
FIG. 4: data transfer between the analytical system and data processing unit

The data transfer between the analytical instrument and data processing unit is illustrated in FIG. 4. As soon as the infrared data transfer module (32) has been inserted in the measuring instrument (40), the instrument is ready to receive and transmit data. Signals can now either be transferred from the PC (43) to the analytical instrument (40) or vice versa. If data are transferred from the PC (43) to the analytical instrument (40), a suitable software is firstly accessed on the PC (43). The PC (43) transmits light impulses in the IR range via its infrared module (44). The data transfer module (32) receives the transmitted light impulses by means of an infrared receiver (33) and converts these into electrical impulses. In this process a light impulse is for example assigned the numerical value 0 and the absence of a light impulse is assigned the numerical value 1. The data are placed on the internal serial bus of the instrument. The data can be used for further processing by the analytical instrument. Hence it is for example possible to provide data processing not only by means of a PC. Also the data obtained from the data processing can for example be used to calibrate new measurement data in the analytical system.

Hence an analytical system having a data transfer module according to the invention can be used in many different ways to manage measurement data which allows an optimization of for example the analytical or treatment methods. The data transfer module which is economical and simple to use facilitates processing of the measurement data for the user.

The invention claimed is:

1. An analytical system comprising:
an analytical instrument having a first slot defining therein an electrical interface and a second slot configured to receive a test element, the analytical instrument measuring a physical characteristic of a bodily fluid deposited on the test element when the test element is inserted into the second slot,
a calibration module separate from the analytical instrument and including a chip having coding stored therein that is specific to a set of the test elements, the calibration module compatible with the first slot of the analytical instrument and contacting the electrical interface in the first slot when the calibration module is inserted into the first slot, the analytical instrument reading the coding stored in the chip and correcting measurements made by the analytical instrument of the physical characteristic of the bodily fluid deposited on any of the set of the test elements based on the coding, and
a data transfer module separate from the analytical instrument and separate from the calibration module, the data transfer module also compatible with the first slot of the analytical instrument and contacting the electrical interface in the first slot when the data transfer module is inserted into the first slot in place of the calibration module, the data transfer module receiving electrical signals from the analytical instrument, converting the electrical signals to electromagnetic or acoustic signals and transferring the electromagnetic or acoustic signals to a data processing unit when the data transfer module is in the first slot and contacting the electrical interface.

2. An analytical system comprising:
an analytical instrument having a first slot defining therein an electrical interface and a second slot configured to receive a test element, the analytical instrument measuring a physical characteristic of a bodily fluid deposited on the test element when the test element is inserted into the second slot,
a calibration module separate from the analytical instrument and including a chip having coding stored therein that is specific to a set of the test elements, the calibration module compatible with the first slot of the analytical instrument and contacting the electrical interface in the first slot when the calibration module is inserted into the first slot, the analytical instrument reading the coding stored in the chip and correcting measurements made by the analytical instrument of the physical characteristic of the bodily fluid deposited on any of the set of the test elements based on the coding, and
a data transfer module separate from the analytical instrument and separate from the calibration module, the data transfer module also compatible with the first slot of the analytical instrument and contacting the electrical interface in the first slot when the data transfer module is inserted into the first slot in place of the calibration module, the data transfer module receiving electromagnetically or acoustically transmitted signals, converting the electromagnetically or acoustically transmitted signals to electrical signals and transferring the electrical signals to the analytical instrument when the data transfer module is in the first slot and contacting the electrical interface.

3. An analytical system comprising:
an analytical instrument having a first slot defining therein an electrical interface and a second slot configured to receive a test element, the analytical instrument measuring a physical characteristic of a bodily fluid deposited on the test element when the test element is inserted into the second slot,
a calibration module separate from the analytical instrument and including a chip having coding stored therein that is specific to a set of the test elements, the calibration module compatible with the first slot of the analytical instrument and contacting the electrical interface in the first slot when the calibration module is inserted into the first slot, the analytical instrument reading the coding stored in the chip and correcting measurements made by the analytical instrument of the physical characteristic of the bodily fluid deposited on any of the set of the test elements based on the coding, and
a data transfer module separate from the analytical instrument and separate from the calibration module, the data transfer module also compatible with the first slot of the analytical instrument and contacting the electrical interface in the first slot when the data transfer module is inserted into the first slot in place of the calibration module, the data transfer module receiving first electrical signals from the analytical instrument, converting the first electrical signals to first electromagnetic or acoustic signals and transferring the first electromagnetic or acoustic signals to a data processing unit when the data transfer module is in the first slot and contacting the electrical interface, the data transfer module receiving second electromagnetically or acoustically transmitted signals, converting the second electromagnetically or acoustically transmitted signals to second electrical signals and transferring the second electrical signals to the analytical instrument when the data transfer module is in the first slot and contacting the electrical interface.

4. The system of claim 1 wherein the physical characteristic of a bodily fluid measured by the analytical instrument is glucose concentration of samples deposited on any of the set of the test elements.

5. The system of claim 1 wherein the data transfer module obtains operating energy from the analytical instrument.

6. The system of claim 1 wherein the data transfer module includes an energy source from which the data transfer module operates.

7. The system of claim 1 wherein the data transfer module comprises a radio module and is a component of a transponder system.

8. The system of claim 1 wherein the electromagnetic signals are optical signals.

9. The system of claim 1 wherein the electromagnetic signals are radio frequency signals.

10. The system of claim 1 wherein the data transfer module is operable to convert the electrical signals to electromagnetic signals and to acoustic signals.

11. The system of claim 1 wherein the data transfer module is operable to convert the electrical signals to electromagnetic signals,
and wherein the electromagnetic signals comprise radio frequency signals and infrared signals.

12. The system of claim 2 wherein the physical characteristic of a bodily fluid measured by the analytical instrument is glucose concentration of samples deposited on any of the set of the test elements.

13. The system of claim 2 wherein the data transfer module obtains operating energy from the analytical instrument.

14. The system of claim 2 wherein the data transfer module includes an energy source from which the data transfer module operates.

15. The system of claim 2 wherein the data transfer module comprises a radio module and is a component of a transponder system.

16. The system of claim 2 wherein the electromagnetically transmitted signals are optical signals.

17. The system of claim 2 wherein the electromagnetically transmitted signals are radio frequency signals.

18. The system of claim 2 wherein the data transfer module is operable to receive electromagnetically and acoustically transmitted signals and to convert the electromagnetically and acoustically transmitted signals to the electrical signals.

19. The system of claim 2 wherein the electromagnetically received signals comprise radio frequency signals and infrared signals, and wherein the data transfer module is operable to convert that radio frequency signals and the infrared signals to the electrical signals.

* * * * *